(12) United States Patent
Kodandaswamy et al.

(10) Patent No.: US 11,864,902 B1
(45) Date of Patent: Jan. 9, 2024

(54) METHODS AND SYSTEMS FOR CLASSIFYING A HEARTBEAT ASSOCIATED WITH PATIENTS IN SINUS RHYTHM

(71) Applicant: Neucures Inc., Los Angeles, CA (US)

(72) Inventors: Chandan Chikkanayakanahally Kodandaswamy, Tumakuru (IN); Nandeesha Gowdagere Madalingaiah, Ramanagara (IN); Rohit Jain, Danville, CA (US)

(73) Assignee: NEUTRACE, INC., Longwood, FL (US)

( * ) Notice: Subject to any disclaimer, the term of this patent is extended or adjusted under 35 U.S.C. 154(b) by 0 days.

(21) Appl. No.: 17/339,999

(22) Filed: Jun. 5, 2021

(51) Int. Cl.
*A61B 5/367* (2021.01)
*A61B 5/283* (2021.01)
*A61B 5/35* (2021.01)
*A61B 5/00* (2006.01)

(52) U.S. Cl.
CPC .............. *A61B 5/367* (2021.01); *A61B 5/283* (2021.01); *A61B 5/35* (2021.01); *A61B 5/746* (2013.01)

(58) Field of Classification Search
CPC ................................ A61B 5/367; A61B 5/352
See application file for complete search history.

(56) References Cited

U.S. PATENT DOCUMENTS

2020/0196885 A1\* 6/2020 Harlev ................... A61B 5/062

\* cited by examiner

*Primary Examiner* — George R Evanisko
(74) *Attorney, Agent, or Firm* — HM LAW GROUP LLP; Vani Moodley, Esq.

(57) ABSTRACT

Techniques are disclosed to identify if a current chamber being mapped is a target chamber that is desired to be mapped based on the relative position of the local activation time relative to QRS onset. Techniques are also disclosed whereby cardiac data can be labeled to indicate whether a beat was acquired while in the ventricle, or in the atrium.

6 Claims, 9 Drawing Sheets

METHODS AND SYSTEMS FOR CLASSIFYING A HEARTBEAT ASSOCIATED WITH PATIENTS IN SINUS RHYTHM

FIELD

Embodiments of the present invention relate to cardiac mapping.

BACKGROUND

During cardiac mapping, a mapping catheter is inserted into a chamber of the heart in respect of which mapping data is to be acquired. However, while moving said mapping catheter within the chamber in order to acquire the mapping data, the mapping catheter may inadvertently be moved to a location such that it is no longer within said chamber, but within an adjacent chamber.

BRIEF SUMMARY

In one aspect, a method, for electrophysiological mapping of a heart, includes receiving input of a chamber of the heart currently being mapped, detecting if a current mapping location is within said chamber, and providing an alert if the current mapping location is no longer within said chamber.

In another aspect, a method, includes receiving electrical recordings for a heart from a mapping catheter inserted into the heart, calculating a time of onset for ventricular depolarization of the heart, selecting portions of the electrical recordings indicative of a heartbeat, for each selected portion calculating a local activation time, and identifying a chamber of the heart being mapped by the mapping catheter based on the relative position of the local activation time and the time of onset for ventricular depolarization.

In yet another aspect, a method, includes generating template for a target chamber, performing template matching on an incoming cardiac signal to identify each beat in the signal, computing QRS onset, extracting a segment of the cardiac signal around each beat, computing a local activation time within each extracted segment, determining a segment of the global activation window where local activation occurs, and labeling each beat as one of an atrial signal and a ventricle signal based a relative timing of local activation time for each beat relative to QRS onset within each extracted segment.

Other aspects of the invention will be apparent from the detailed description below.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
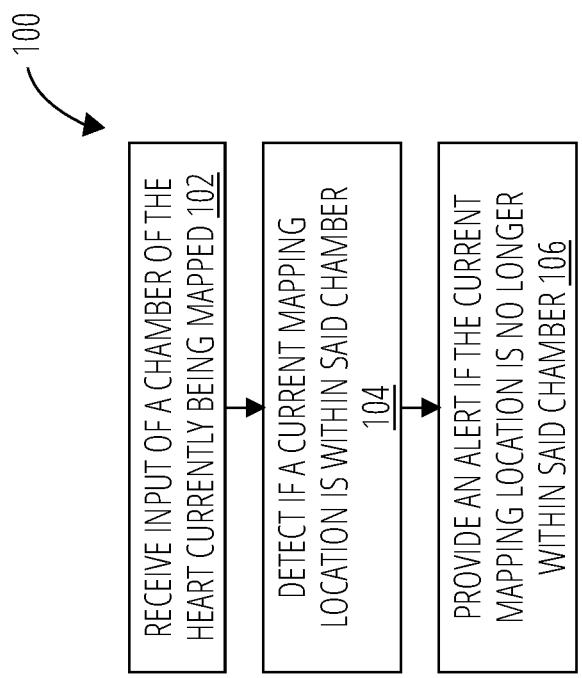
FIG. 1 illustrates a routine 100 in accordance with one embodiment.

The phrases "in one embodiment", "in various embodiments", "in some embodiments", and the like are used repeatedly. Such phrases do not necessarily refer to the same embodiment. The terms "comprising", "having", and "including" are synonymous, unless the context dictates otherwise.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to or combined, without limiting the scope to the embodiments disclosed herein.

As used herein, the term "target chamber" denotes a chamber of a heart that is desired to be mapped.

Broadly, embodiments of the present invention disclose techniques that assist in mapping the target chamber.

According to one embodiment of the invention during a mapping of a target chamber, a notification technique is provided to notify or alert an operator if the current mapping location is no longer within the target chamber.

According to another embodiment of the invention during mapping of the ventricular or atrial chambers of the heart of patients in sinus rhythm, an identification technique is provided to identify the current chamber being mapped by a mapping catheter.

According to yet another embodiment of the invention, a beat classification technique is disclosed where in each beat in the incoming cardiac signal is isolated and analyzed to determine if said beat is part of an atrial signal, or a ventricular signal.

A system for implementing the techniques is also disclosed.

According to one embodiment of the invention during mapping of a target chamber, a notification technique is provided to notify or alert an operator if the current mapping location is no longer within the target chamber.

According to another embodiment of the invention during mapping of the ventricular or atrial chambers of the heart of a patient in sinus rhythm, an identification technique is provided to identify the current chamber being mapped by a mapping catheter.

According to yet another embodiment of the invention, a beat classification technique is disclosed wherein each beat in an incoming cardiac signal is isolated and analyzed to determine if said beat is part of an atrial signal or a ventricular signal.

Although not required, the inventive techniques are described in the general context of computer-program instructions being executed by a computing device 700 (which is described later would reference to FIG. 7) which forms part of a cardiac mapping system 800 (which is described later with respect to FIG. 8).

Program instructions generally include routines, programs, objects, components, data structures, etc., that perform particular tasks or implement particular abstract data types to implement the aforementioned techniques. While the systems and methods are described in the foregoing context, acts and operations described herein after may also be implemented in hardware.

Aspects of the notification technique: In one embodiment, the notification technique may comprise a routine 100 illustrated in FIG. 1. The routine 100 may be performed by the computing device 700 together with the cardiac mapping system 800. Referring to FIG. 1, at block 102 user/operator input is received indicating the target chamber that is desired to be mapped. For example, a user interface may be provided whereby the operator may select a chamber that is the target chamber. At block 104, the routine 100 detects if a current mapping location is within the user-input target chamber. In one embodiment, part of the processing at block 104 includes receiving an intracardiac signal from a mapping catheter inserted into the heart, extracting segments of the intracardiac signal corresponding to each heartbeat, and classifying each signal segment as either an atrial signal or a ventricular signal (as will be described in greater detail later). Once each signal segment is classified, then at block 106 an alert is provided to the operator if the current mapping location is no longer within the target chamber. For example, if the target chamber is the atrial chamber and analysis of the signal segment corresponding to a heartbeat indicates that said signal segment is a ventricular signal, then an alert in the form of an audible alarm may be sounded to indicate that the current chamber being mapped is a ventricular chamber and thus no longer the target chamber. Advantageously, the operator can then take corrective action to move the mapping catheter back into the target chamber. Aspects of segment extraction, and segment classification are described below.

Figure 2:
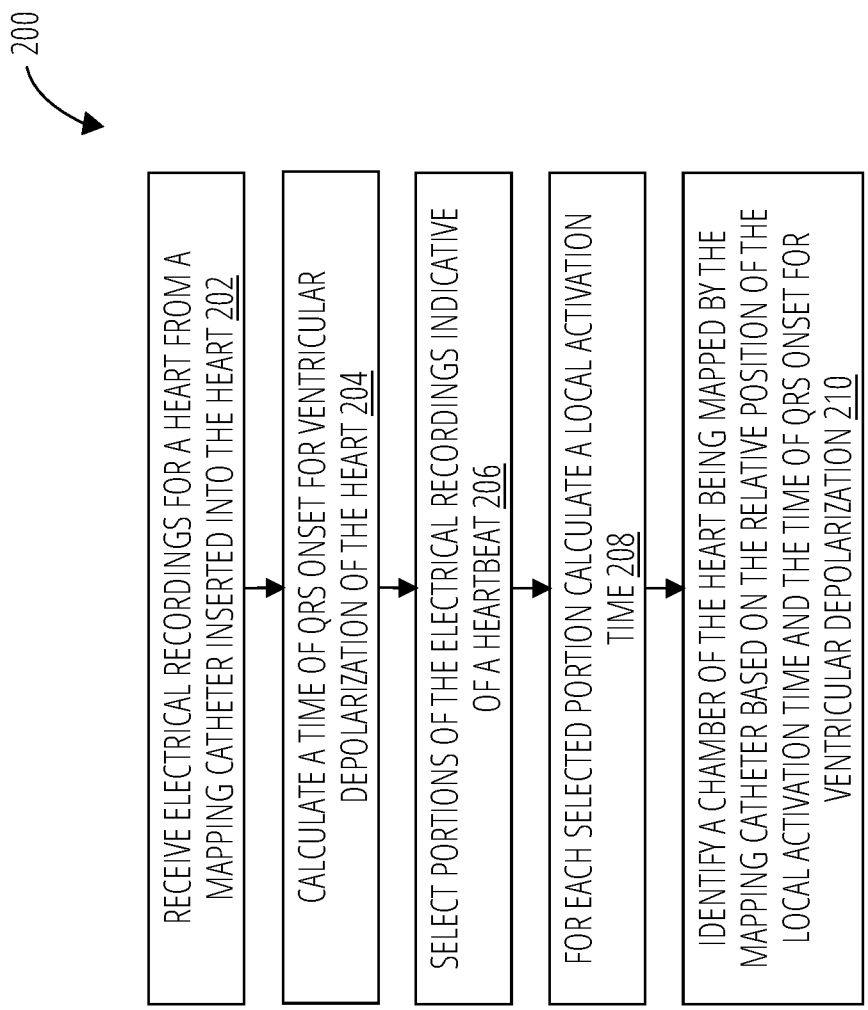
FIG. 2 illustrates a routine 200 in accordance with one embodiment.

Aspects of the identification technique: In one embodiment, the identification technique may comprise a routine 200 illustrated in FIG. 2. The routine 200 may be performed by the computing device 700 together with the cardiac mapping system 800. Referring to FIG. 2, at block 202 electrical signals/recordings for a heart are received from a mapping catheter inserted into the heart. At block 204, a time of QRS onset for ventricular depolarization of the heart is calculated. One technique for calculating the time of QRS onset for ventricular depolarization is described in co-pending US Patent Application Number 174/073, 211 entitled "METHOD AND SYSTEMS FOR DETERMINING QRS ONSET AND CARDIAC SIGNALS", which is incorporated herein by reference. Segments or portions of the electrical signals received from the mapping catheter are then selected at block 206. At block 208, a local activation time corresponding to each selected portion/heartbeat is calculated. One technique for computing the local activation time is disclosed in co-pending U.S. patent application Ser. No. 17/073,220 entitled "METHOD AND SYSTEM FOR MEASURING UNIPOLAR AND BIPOLAR CARDIAC TELEGRAM FRACTIONATION", which is incorporated herein by reference. Thereafter, block 210 executes wherein the particular chamber of the heart currently being mapped is identified. For this step, the identification is based on the relative position of the local activation time calculated at block 208 and the time of QRS onset calculated at block 204. For the identification, if the local activation time occurs before QRS onset, then the corresponding beat is considered an atrial signal and if the local activation time occurs after the QRS onset, then the corresponding beat is considered a ventricle signal. In some embodiments, the intracardiac signal may be labeled in real-time with the label "correct chamber" in cases where it is determined that the current chamber being mapped is the target chamber, and "unknown chamber" if the current chamber being mapped is not the target chamber.

Figure 3:
FIG. 3 illustrates a routine 300 in accordance with one embodiment.

In one embodiment, the beat classification technique may comprise a routine 300 illustrated in FIG. 3. The routine 300 may be performed by the computing device 700 together with the cardiac mapping system 800. Referring to FIG. 3, at block 302 a template is generated for the target chamber.

In one embodiment, the template is generated from a reference signal selected by the electrophysiologist performing the mapping procedure from the body surface ECG leads. Essentially, the electrophysiologist chooses a reference signal for the target chamber, for example, the lead V3 or V4 of the ECG system. Criteria for choosing the reference may include the stability and noise characteristics of the signal.

Figure 4:
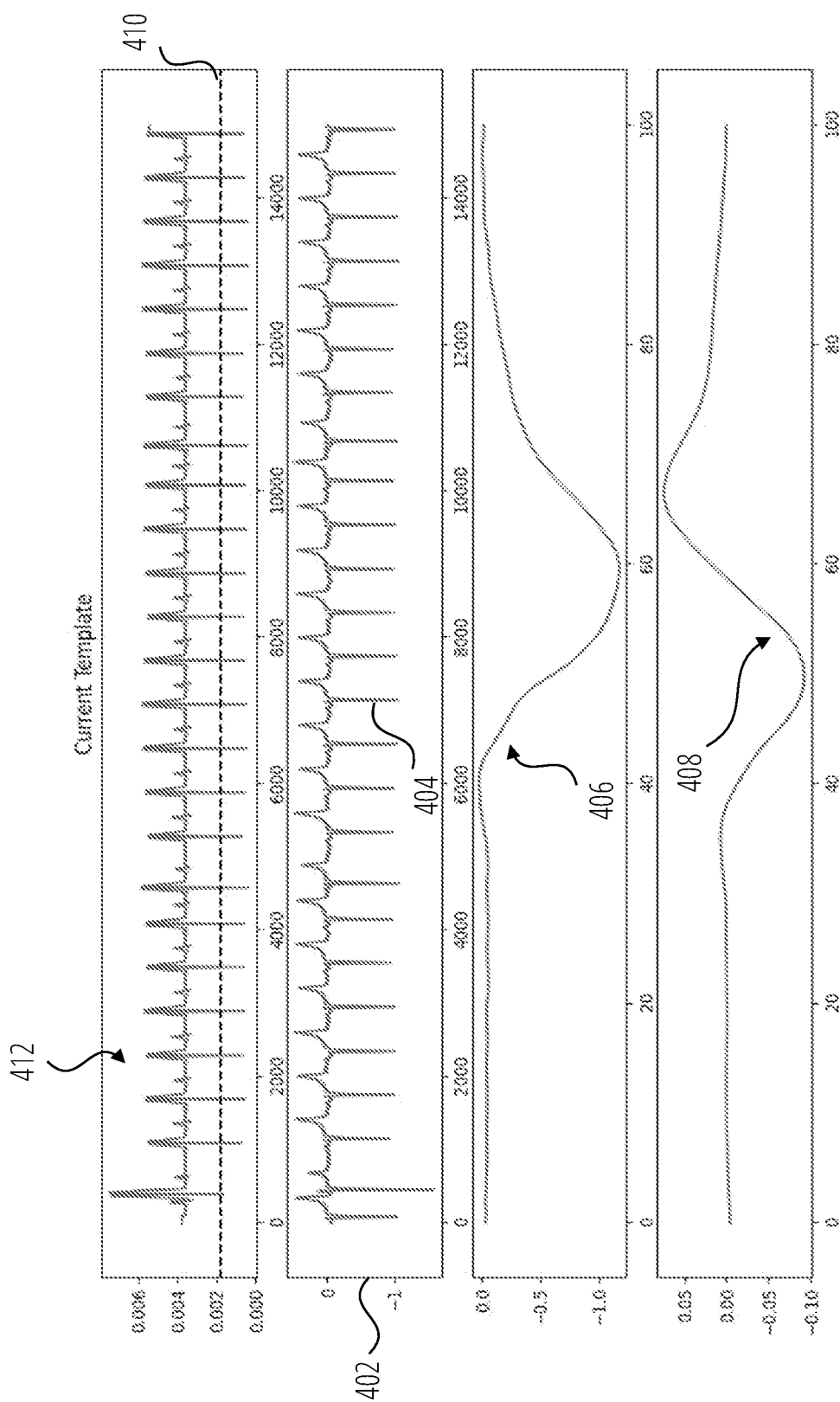
FIG. 4 illustrates an aspect of the subject matter in accordance with one embodiment.

In one embodiment, in order to generate the template, 15 to 20 seconds of incoming signals transmitted on the reference lead may be collected. Referring to FIG. 4 of the drawings, reference numeral 402 indicates 15 seconds of data used for template generation. As can be seen, the data 402 comprises a series of downward deflections 404. For template generation, in accordance with one embodiment, the sharpest downward deflection is selected from the 15 seconds of data. Next a window of say 101 milliseconds is created around the selected sharpest downward deflection, and that portion of the data 402 is extracted. This is indicated by reference numeral 406 in FIG. 4. Thereafter, the time derivative of the extracted portion 406 is calculated. The time derivative is indicated by reference numeral 408 and defines the template.

Figure 5:
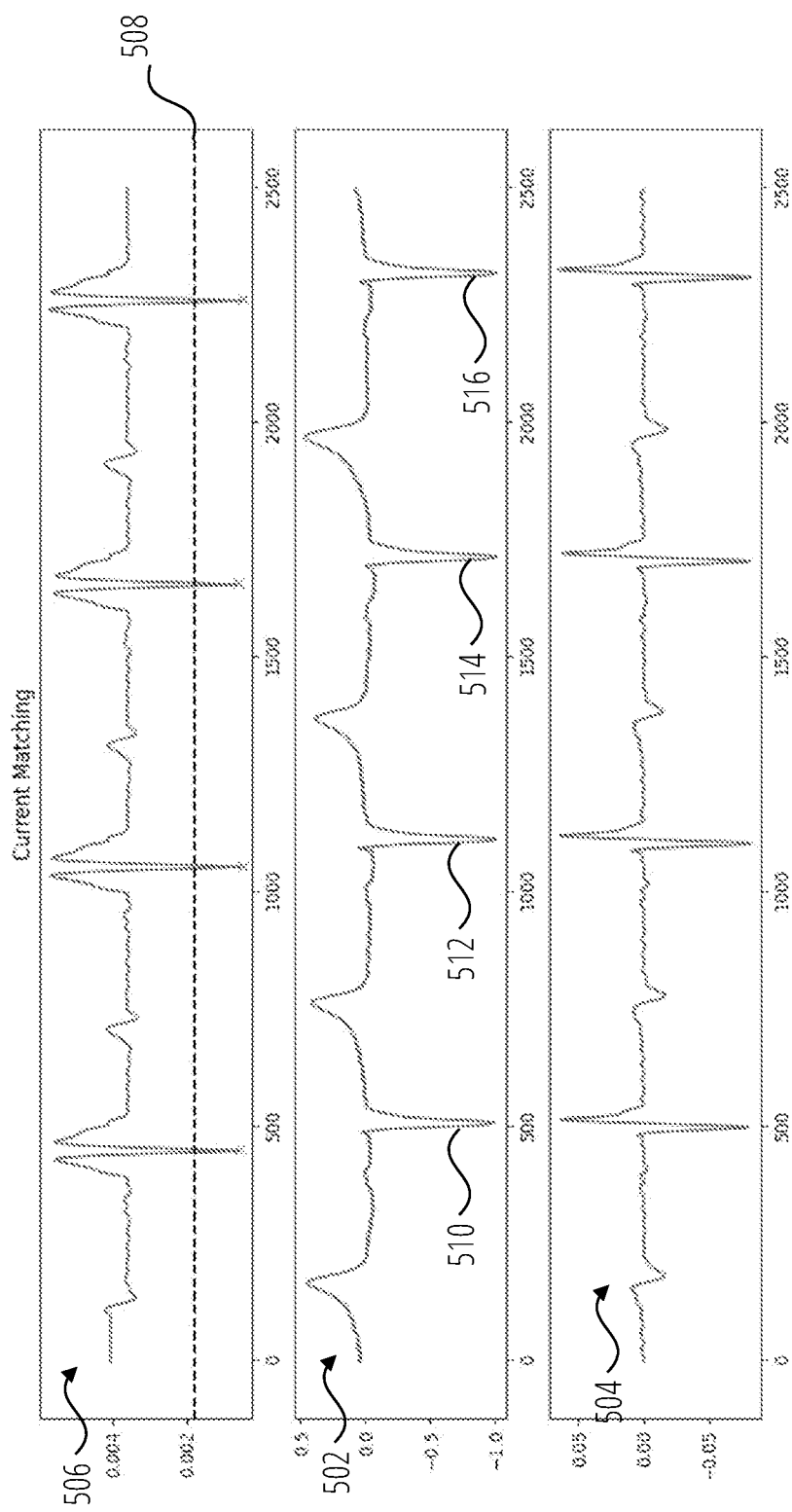
FIG. 5 illustrates an aspect of the subject matter in accordance with one embodiment.

Referring again to FIG. 3 of the drawings, the next step in the beat classification technique comprises block 304 wherein template matching is performed on the incoming intracardiac signals to identify each heartbeat in the signal. Template matching in accordance with one embodiment of the invention is illustrated in FIG. 5 of the drawings. Referring to FIG. 5, an incoming intracardiac signal 502 is matched against template 508. The template 508 is generated in accordance with the techniques described above and is effectively the first derivative with respect to the time of the signal 502. The match occurs when the template 504 is aligned with the signal 502, and the downward deflection exceeds the threshold 508. As will be seen, for the signal 502, and match occurs at four locations in the signal. The temporal location in the signal at which the match occurs is the location of the beat and beat extraction involves extracting a segment or portion of the intracardiac signal centered on each beat. For template matching, a certain threshold is selected, for example for 50% of the median value of the reference signal. In one embodiment, each downward deflection in the incoming intracardiac signal is considered to be a beat if the magnitude of the downward deflection exceeds the threshold. Reference 410 in FIG. 4 of the drawings indicates the selected threshold, in accordance with one embodiment of the invention. In one embodiment, each portion/segment of the incoming intracardiac signal is matched using the template 408 and the threshold 410 to build a match function 412. As will be seen, the match function has matched a series of beats which are indicated by those portions of the graph where the downward deflection crosses the threshold 410. In one embodiment, the match function is configured to check the alignment between the template 408 and the incoming intracardiac signal 402. When there is alignment between the signal and, the downward deflection in the signal falls below the threshold the time of said downward deflection correlates with a beat in the signal. As will be seen, the location of the four beats that were identified in accordance with the above technique correlates with the minimum points of the match function 506. For matching, and according to one embodiment, the incoming intracardiac signal 502 is subtracted from the template 504 sample-by-sample and those portions of the resultant signal 506 are considered matched if they exceed the threshold 508. In FIG. 5, the beats are indicated by reference numerals 510-516.

Next, at block 308, a segment of the incoming intracardiac signal 502 centered on each identified beat is extracted. In one embodiment, each segment may include 300 milliseconds of data centered on each beat. For ease of reference, the extracted segment will be referred to herein as the "global activation window". Note that the reference signals and the incoming intracardiac signals at the time aligned thus making it easy to determine the location of the beats in the intracardiac signal. For the example of FIG. 5, four segments will be extracted.

Within each global activation window, the QRS onset is computed at block 308 and the local activation time is computed at block 310. The manner of QRS computation and local activation time computation may be according to the techniques of the co-pending applications incorporated herein by reference, in accordance with one embodiment.

Next, at block 312, the particular segment within the global activation window within which the local activation occurs is determined. In this regard the global activation is considered to comprise two segments —a segment prior to QRS onset and a segment after QRS onset.

Figure 6:
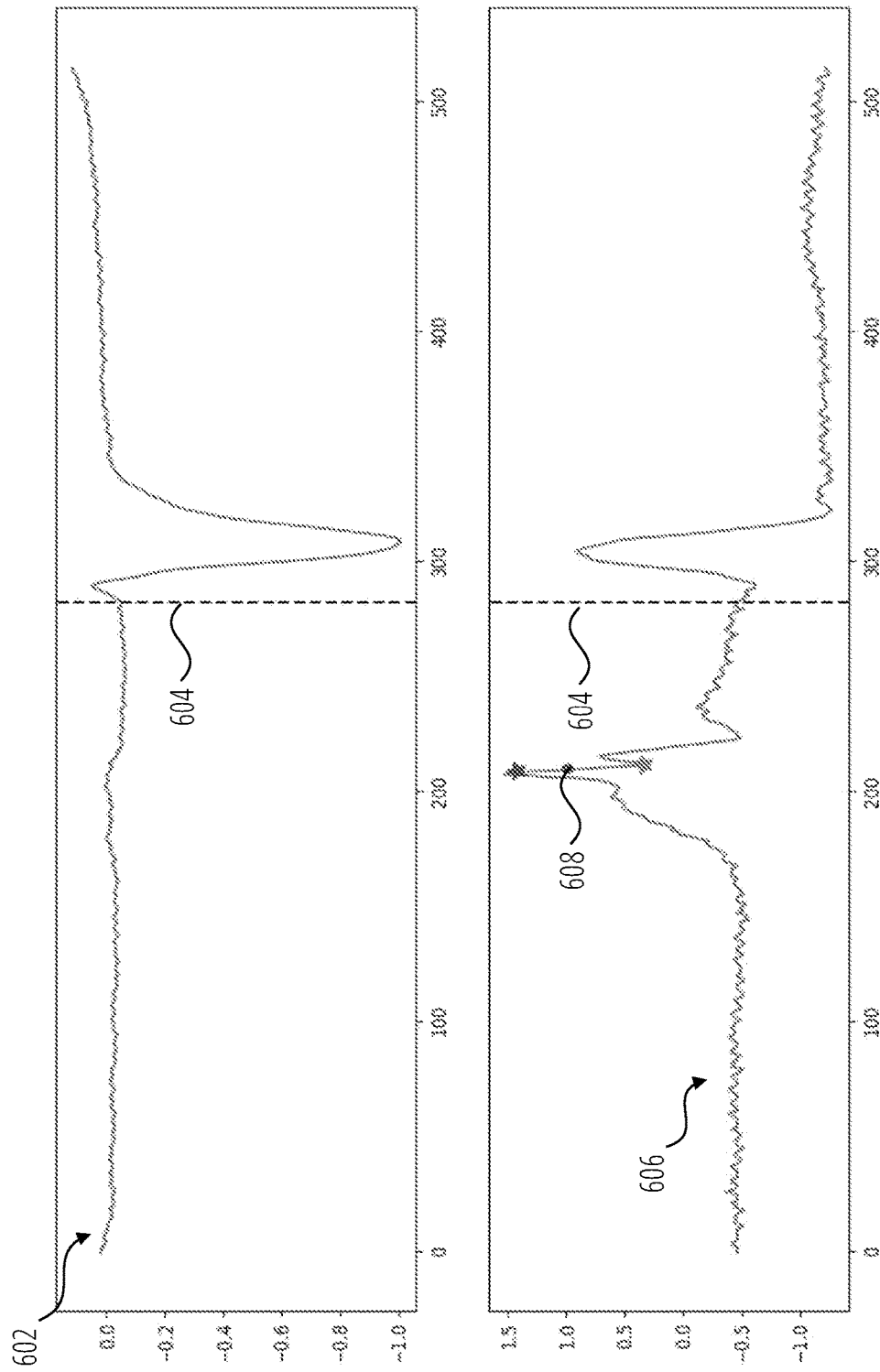
FIG. 6 illustrates an aspect of the subject matter in accordance with one embodiment.

At block 314, based on the relative timing of the local activation time relative to QRS onset, each beat may be labeled as being one of an atrial signal and a ventricular signal as will be explained with reference to FIG. 6 of the drawings. Referring to FIG. 6, reference FIG. 2 indicates a portion of the reference ECG that is centered on the QRS onset 604. To be clear, the signal 602 comprises hundred and 50 milliseconds of data prior to the occurrence of the QRS onset, and 150 milliseconds of data after the occurrence of the QRS onset. Reference numeral 606 indicates a time aligned segment of the intracardiac signal (time aligned with respect to the signal 602). The local activation time is computed for the segment 606 and is indicated by reference numeral 608. As will be seen, the local activation time 608 occurs in the segment prior to the QRS onset signal for. This is indicative of an atrial signal. In contrast if the local activation time occurred in the segment after the QRS onset 604 this condition would be indicative of a ventricular signal. Thus, based on the relative timing of the local activation time relative to the time of QRS onset, one can label a beat as being of the ventricular or atrial origin.

Although not required, the inventive techniques are described in the general context of computer-program instructions being executed by a computing device. Program instructions generally include routines, programs, objects, components, data structures, etc., that perform the particular tasks or implement particular abstract data types. While the systems and methods are described in the foregoing context, acts and operations described herein after may also be implemented in hardware.

Figure 7:
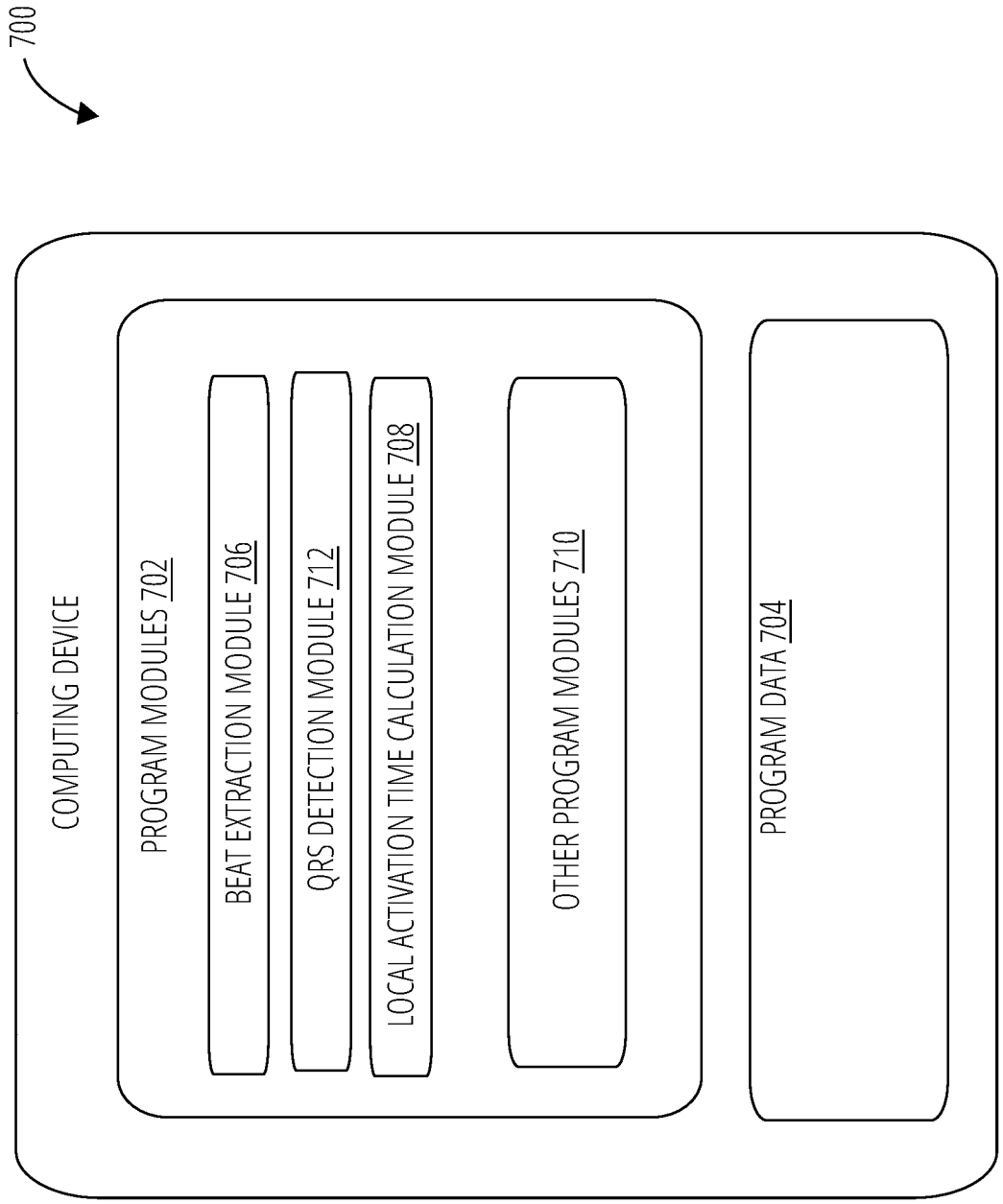
FIG. 7 illustrates one embodiment of high-level block diagram of a computing device for practicing aspects of the invention.

FIG. 7 shows an exemplary system in the form of a computing device 700 for implementing the techniques disclosed herein, in accordance with one embodiment of the invention. Computing device 700 may represent any type of computing device such as a laptop, server, etc. Computing device 700 comprises program modules 702 and program data 704. Program modules 702 may comprise, for example, beat extraction module 706, local activation time calculation module 708 and other program modules 710 such as an operating system, etc.

In use, computing device 700 may form part of a cardiac mapping system 800 (which is described later with reference to FIG. 8) configured to receive electrocardiogram (ECG) signals and electrophysiological data for a heart. Cardiac mapping system 800 is operable to first select a set of surface electrodes which are then driven with current pulses. While the current pulses are being delivered, electrical activity, such as the voltage is measured with at least one of the remaining surface electrodes and in vivo electrodes and stored.

In accordance with one embodiment of the invention, cardiac mapping system 800 also includes an electrocardiogram system (not shown) to generate electrocardiograms (ECGs) for a patient. The system 800 also generates electrophysiological (EP) data in the form of EP data points each comprising a recording location within the heart (specified in terms of X, Y, and Z coordinates) and a voltage reading recorded at said location. Thus, each voltage measurement may be associated with position data comprising the spatial location within the heart at which the voltage measurement was made.

Figure 8:
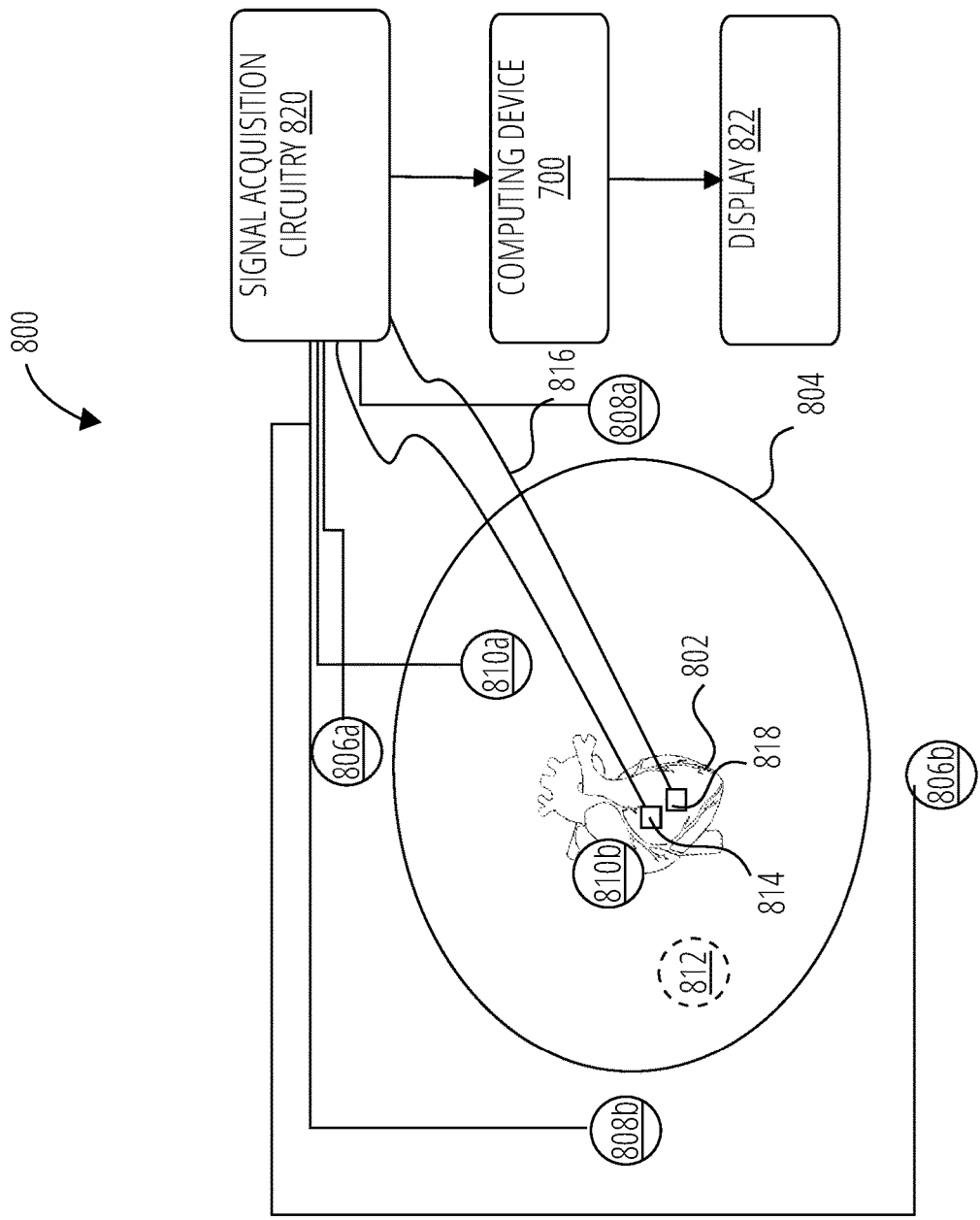
FIG. 8 illustrates an embodiment of a mapping system which may be used to implement aspects of the techniques disclosed herein.

FIG. 8, which shows a schematic diagram of a cardiac mapping system 800 for conducting cardiac electrophysiology studies by navigating a cardiac catheter and measuring electrical activity occurring in a heart 802 of a patient 804 and three-dimensionally mapping the electrical activity and/or information related to or representative of the electrical activity. Cardiac mapping system 800 can be used to help create an anatomical model using one or more electrodes. Cardiac mapping system 800 can also be used to measure electrophysiology data at a plurality of points along a cardiac surface, and store the measured data in association with location information for each measurement point at which the electrophysiology data was measured.

The cardiac mapping system 800 comprises a computing device 700, X-axis surface electrodes 706a, 706b, Y-axis surface electrodes 708a, 708b, Z-axis surface electrodes 710a, 710b, surface reference electrode 812, fixed intra-cardiac electrode 814, mapping catheter 816, mapping electrode 818, signal acquisition circuitry 820, and a display 822.

The surface electrodes (e.g., patch electrodes) are shown applied to a surface of patient 804 along an X-axis, a Y-axis, and a Z-axis. Surface reference electrode 812 provides a reference and/or ground electrode for the cardiac mapping system 800. Surface reference electrode 812 may be an alternative to fixed intra-cardiac electrode 814. It should also be appreciated that, in addition, the patient 804 will have most or all of the conventional electrocardiogram (ECG) system leads in place. This ECG information is available to cardiac mapping system 800 although not illustrated in the FIG. 8.

In one embodiment, the localization/mapping system is the EnSite NavX™ navigation and visualization system of St. Jude Medical, Atrial Fibrillation Division, Inc. Other localization systems, however, may be used in connection with the present invention, including for example, the CARTO navigational and location system of Biosense Webster, Inc. and the LOCALISA intracardiac navigation system of Medtronic, Inc. The localization and mapping systems described in the following patents (all of which are hereby incorporated by reference in their entireties) can be used with the present invention: U.S. Pat. Nos. 6,990,370; 6,978, 168; 6,947,785; 6,939,309; 6,728,562; 6,640,119; and 5,983, 126.

Each surface electrode is coupled to the multiplex switch of signal acquisition circuitry 820 and the pairs of electrodes are selected by software running on computing device 700, which couples the electrodes to a signal generator of the signal acquisition circuitry 820. Computing device 700, for example, may comprise a conventional general-purpose computer, a special-purpose computer, a distributed computer, or any other type of computer. The computing device 700 may comprise one or more processors, such as a single central-processing unit, or a plurality of processing units, commonly referred to as a parallel processing environment.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across a fixed intra-cardiac electrode 814 resulting from a predetermined set of drive (source-sink) configurations are combined algebraically to yield the same effective potential as would be obtained by simply driving a uniform current along the orthogonal axes.

Any two of the surface electrodes may be selected as a dipole source and drain with respect to a ground reference, e.g., the surface reference electrode 812 while the unexcited electrodes measure voltage with respect to the ground reference. The mapping/measurement electrode 818 placed in the heart 802 is exposed to the field from a current pulse and is measured with respect to ground, e.g., the surface reference electrode 812. In practice the catheters within the heart may contain multiple electrodes and each electrode potential may be measured. As previously noted, at least one electrode may be fixed to the interior surface of the heart to form a fixed intra-cardiac electrode 814, which is also measured with respect to ground. Data sets from each of the surface electrodes, the internal electrodes, and the virtual electrodes may all be used to determine the location of the measurement electrode 818 or other electrodes within the heart 802.

In summary, the cardiac mapping system 800 first selects a set of surface electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the cardiac mapping system 800 that are associated with multiple electrode locations (e.g., endocardial electrode locations). Each point in the set has coordinates in space.

Figure 9:
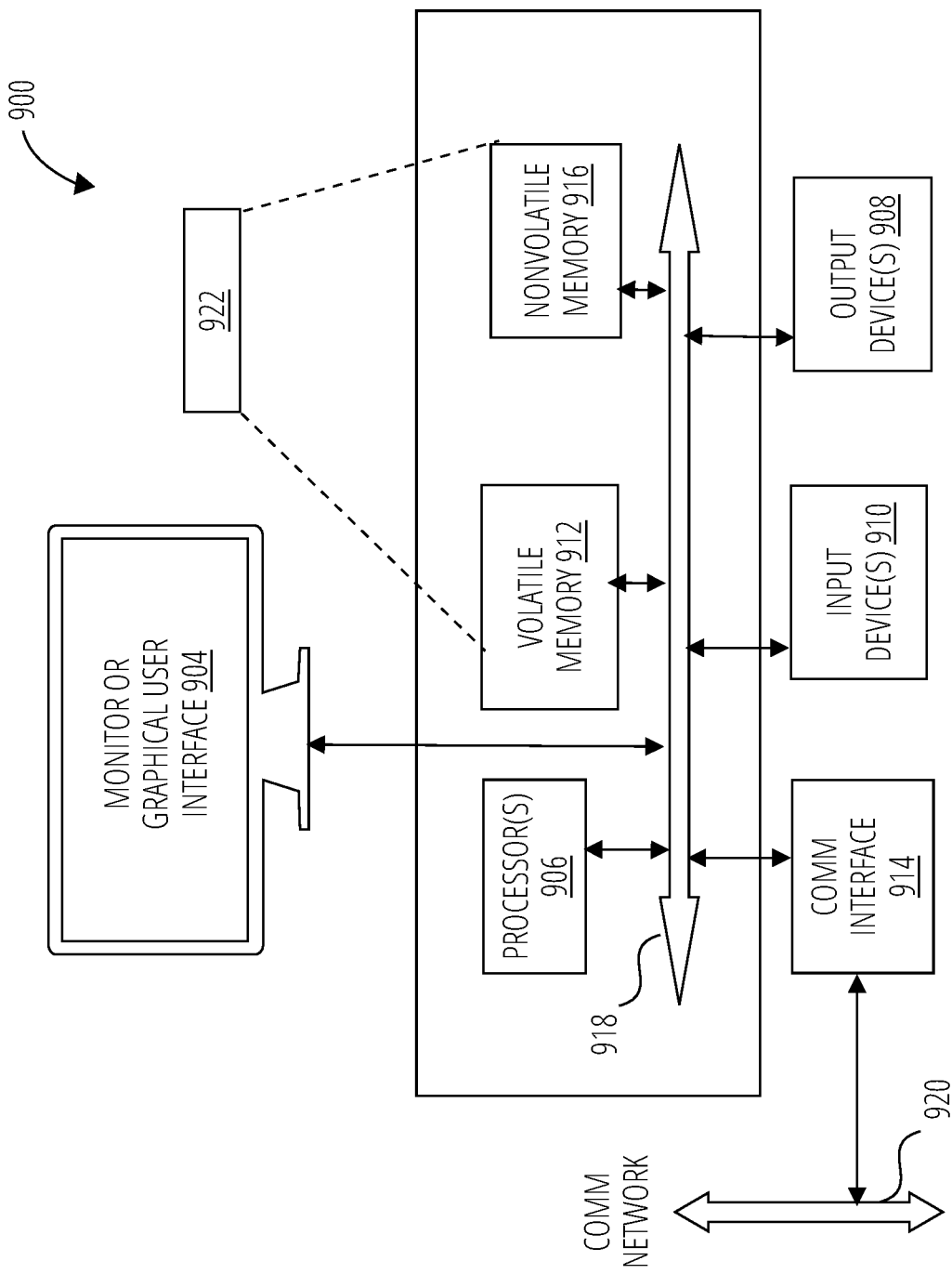
FIG. 9 illustrates a high-level block diagram of exemplary hardware for the computing device 700.

FIG. 9 is an example block diagram of hardware for the computing device 700 in accordance with one embodiment of the present invention. FIG. 9 is merely illustrative of a machine system to carry out aspects of the technical processes described herein, and does not limit the scope of the claims. One of ordinary skill in the art would recognize other variations, modifications, and alternatives. In one embodiment, the computing device 700 typically includes a monitor or graphical user interface 904, a data processing system 902, a communication network interface 914, input device(s) 910, output device(s) 908, and the like.

As depicted in FIG. 9, the data processing system 902 may include one or more processor(s) 906 that communicate with a number of peripheral devices via a 918 These peripheral devices may include input device(s) 910, output device(s) 908, communication network interface 914, and a storage subsystem, such as a volatile memory 912 and a nonvolatile memory 916.

The volatile memory 912 and/or the nonvolatile memory 916 may store computer-executable instructions and thus forming logic 922 that when applied to and executed by the processor(s) 906 implement embodiments of the processes disclosed herein.

The input device(s) 910 include devices and mechanisms for inputting information to the data processing system 902. These may include a keyboard, a keypad, a touch screen incorporated into the monitor or graphical user interface 904, audio input devices such as voice recognition systems, microphones, and other types of input devices. In various embodiments, the input device(s) 910 may be embodied as a computer mouse, a trackball, a track pad, a joystick, wireless remote, drawing tablet, voice command system, eye tracking system, and the like. The input device(s) 910 typically allow a user to select objects, icons, control areas, text and the like that appear on the monitor or graphical user interface 904 via a command such as a click of a button or the like.

The output device(s) 908 include devices and mechanisms for outputting information from the data processing system 902. These may include the monitor or graphical user interface 904, speakers, printers, infrared LEDs, and so on as well understood in the art.

The communication network interface 914 provides an interface to communication networks (e.g., communication network 920) and devices external to the data processing system 902. The communication network interface 914 may serve as an interface for receiving data from and transmitting data to other systems. Embodiments of the communication network interface 914 may include an Ethernet interface, a modem (telephone, satellite, cable, ISDN), (asynchronous) digital subscriber line (DSL), FireWire, USB, a wireless communication interface such as BlueTooth or WiFi, a near field communication wireless interface, a cellular interface, and the like.

The communication network interface 914 may be coupled to the communication network 920 via an antenna, a cable, or the like. In some embodiments, the communication network interface 914 may be physically integrated on a circuit board of the data processing system 902, or in some cases may be implemented in software or firmware, such as "soft modems", or the like.

The computing device 900 may include logic that enables communications over a network using protocols such as HTTP, TCP/IP, RTP/RTSP, IPX, UDP and the like.

The volatile memory 912 and the nonvolatile memory 916 are examples of tangible media configured to store computer readable data and instructions to implement various embodiments of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 912 and the nonvolatile memory 916 may be configured to store the basic programming and data constructs that provide the functionality of the disclosed processes and other embodiments thereof that fall within the scope of the present invention.

Logic 922 that implements embodiments of the present invention may be stored in the volatile memory 912 and/or the nonvolatile memory 916. Said logic 922 may be read from the volatile memory 912 and/or nonvolatile memory 916 and executed by the processor(s) 906. The volatile memory 912 and the nonvolatile memory 916 may also provide a repository for storing data used by the logic 922.

The volatile memory 912 and the nonvolatile memory 916 may include a number of memories including a main random-access memory (RAM) for storage of instructions and data during program execution and a read only memory (ROM) in which read-only non-transitory instructions are stored. The volatile memory 912 and the nonvolatile memory 916 may include a file storage subsystem providing persistent (non-volatile) storage for program and data files. The volatile memory 912 and the nonvolatile memory 916 may include removable storage systems, such as removable flash memory.

The bus subsystem 918 provides a mechanism for enabling the various components and subsystems of data processing system 902 communicate with each other as intended. Although the communication network interface 914 is depicted schematically as a single bus, some embodiments of the bus subsystem 918 may utilize multiple distinct busses.

It will be readily apparent to one of ordinary skill in the art that the computing device 900 may be a device such as a smartphone, a desktop computer, a laptop computer, a rack-mounted computer system, a computer server, or a tablet computer device. As commonly known in the art, the computing device 900 may be implemented as a collection of multiple networked computing devices. Further, the computing device 900 will typically include operating system logic (not illustrated) the types and nature of which are well known in the art.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non-transitory machine readable media, and/or circuitry which by way of its material and/or material-energy configuration comprises control and/or procedural signals, and/ or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

What is claimed is:

1. A method, comprising:
   inserting a mapping catheter into a heart of a subject;
   driving body surface electrodes with current pulses;
   measuring electrical recordings for the heart using the mapping catheter inserted into the heart and due to the driven current pulses;
   calculating a time of QRS onset for ventricular depolarization of the heart;
   selecting portions of the electrical recordings indicative of a heartbeat;
   calculating, for each selected portion, a local activation time; and
   identifying a chamber of the heart based on a relative position of the local activation time and the time of QRS onset for ventricular depolarization, wherein
      the chamber of the heart is identified as an atrial chamber when the local activation time is earlier than the QRS onset, and
      the chamber of the heart is identified as a ventricular chamber when the local activation time is later than the QRS onset.

2. The method of claim 1, wherein
   the method further comprises generating a template for the heartbeat.

3. The method of claim 2, wherein
   to select the portions of the electrical recordings indicative of the heartbeat, the method further comprises performing template matching based on the generated template and the electrical recordings.

4. The method of claim 3, further comprising:
measuring an electrocardiogram;
selecting a heartbeat in the electrocardiogram; and
generating the template from the selected heartbeat in the electrocardiogram.

5. The method of claim 4, wherein the electrocardiogram is for a reference lead.

6. The method of claim 5, wherein selecting the heartbeat in the electrocardiogram comprises selecting a portion of the electrocardiogram where a time derivative of the portion is a minimum and the portion exceeds a threshold magnitude.

\* \* \* \* \*